United States Patent
Papp et al.

(10) Patent No.: US 9,115,069 B2
(45) Date of Patent: Aug. 25, 2015

(54) PROCESS FOR HYDROFORMYLATION OF OLEFINS

(71) Applicant: BASF SE, Ludwigshafen (DE)

(72) Inventors: Rainer Papp, Speyer (DE); Jens Rudolph, Ludwigshafen (DE); Hans-Günter Thelen, Mannheim (DE); Klaus Diehl, Deer Park, TX (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/542,855

(22) Filed: Nov. 17, 2014

(65) Prior Publication Data

US 2015/0141702 A1 May 21, 2015

Related U.S. Application Data

(60) Provisional application No. 61/905,301, filed on Nov. 18, 2013.

(51) Int. Cl.
*C07C 45/50* (2006.01)

(52) U.S. Cl.
CPC ........................... *C07C 45/50* (2013.01)

(58) Field of Classification Search
CPC ...................................... C07C 45/50
USPC ........................................... 568/451
See application file for complete search history.

(56) References Cited

U.S. PATENT DOCUMENTS

| | | |
|---|---|---|
| 3,830,846 A | 8/1974 | Duembgen et al. |
| 3,932,523 A | 1/1976 | Strohmeyer et al. |
| 6,015,928 A | 1/2000 | Gubisch et al. |
| 6,723,884 B1 | 4/2004 | Grenacher et al. |
| 8,138,379 B2 | 3/2012 | Lueken et al. |
| 8,680,353 B2 | 3/2014 | Crone et al. |
| 2003/0032843 A1 | 2/2003 | Drees et al. |
| 2014/0155656 A1 | 6/2014 | Krokoszinski et al. |

FOREIGN PATENT DOCUMENTS

| | | |
|---|---|---|
| DE | 1205514 B | 11/1965 |
| DE | 1938102 A1 | 3/1972 |
| DE | 2404855 A1 | 8/1975 |
| EP | 0850905 A1 | 7/1998 |
| EP | 1204624 A1 | 5/2002 |
| EP | 1279658 A2 | 1/2003 |
| GB | 1079209 A | 8/1967 |
| WO | WO-2009/080396 A1 | 7/2009 |

*Primary Examiner* — Sikarl Witherspoon

(74) *Attorney, Agent, or Firm* — Drinker Biddle & Reath LLP

(57) ABSTRACT

In the hydroformylation of olefins having 6 to 20 carbon atoms in the presence of a cobalt catalyst in the presence of an aqueous phase with thorough mixing in a reactor, a hydroformylation products-containing first stream is withdrawn at the top of the reactor and an aqueous phase-containing second stream is withdrawn from the bottom of the reactor. The flow rate of the second stream is controlled in accordance with a temperature which is measured at a point in the bottom of the reactor or in a line leading out of the bottom of the reactor. The yield of crude hydroformylation product is increased as a result of stable sustained operation.

13 Claims, 2 Drawing Sheets

PROCESS FOR HYDROFORMYLATION OF OLEFINS

CROSS-REFERENCE TO RELATED APPLICATIONS

This application claims priority to U.S. Application No. 61/905,301, filed Nov. 18, 2013, which is incorporated by reference herein in its entirety.

FIELD OF THE INVENTION

The present invention relates to a process for hydroformylation of olefins having 6 to 20 carbon atoms.

BACKGROUND OF THE INVENTION

Hydroformylation or the oxo process is an important large-scale industrial process for preparing aldehydes from olefins, carbon monoxide and hydrogen. These aldehydes can optionally be hydrogenated with hydrogen in the same operation or subsequently in a separate hydrogenation step, to produce the corresponding alcohols. Hydroformylation is carried out in the presence of catalysts which are homogeneously dissolved in the reaction medium. Catalysts used are generally the carbonyl complexes of metals of transition group VIII, in particular Co, Rh, Ir, Pd, Pt or Ru, which may be unmodified or modified with, for example, amine-containing or phosphine-containing ligands. A summarizing account of the processes practiced on a large scale in industry is found in J. Falbe, "New Syntheses with Carbon Monoxide", Springer Verlag 1980, p. 162 ff.

While short-chain olefins with up to 5 carbon atoms are currently predominantly hydroformylated using ligand-modified rhodium carbonyls as the catalyst, cobalt remains the dominant catalytically active central atom for longer-chained olefins. This is due, firstly, to the high catalytic activity of the cobalt carbonyl catalyst irrespective of the position of the olefinic double bonds, the branch structure and the purity of the olefin to be reacted. Secondly, the cobalt catalyst can be separated off from the hydroformylation products and recycled into the hydroformylation reaction relatively easily. Additionally, catalyst losses during working up can be tolerated more easily owing to the lower price of cobalt.

In one customary process for separating off and recycling the cobalt catalyst, the organic phase of the reactor affluent is freed of cobalt carbonyl complexes by treatment with oxygen or air in the presence of weakly acidic water (cf. DE-AS 24 04 855). In the treatment, the cobalt catalyst is destroyed by oxidation and the central atom is formally converted from the oxidation state −1 to +2 and can then be removed by extraction with the aqueous solution (decobalting). The catalyst complex required for hydroformylation can be re-formed from the cobalt(II) salt solution by reaction with carbon monoxide and hydrogen (carbonyl formation). The re-formed cobalt catalyst is then extracted from the aqueous phase with an organic phase, preferably the olefin to be hydroformylated (catalyst extraction). Besides the olefin, the reaction products and by-products of the hydroformylation can also be used for catalyst extraction. The olefins loaded with the cobalt catalyst are then hydroformylated in a reactor at elevated pressure and elevated temperature (olefin hydroformylation).

The reaction output is customarily withdrawn at the top of the reactor, in particular when a vertical tubular reactor is used. Particularly with higher olefins having 8 carbon atoms or more, the aqueous phase supplied to the reaction zone and necessary to achieve a sufficient catalyst concentration in the reaction zone is not entirely discharged in dissolved or suspended form with the reaction mixture removed from the top. Therefore, reaction output is preferably removed not only at the top, but also from the bottom space.

The uncontrolled or insufficiently controlled withdrawal of aqueous phase from the bottom space leads to operational disruption. An excess of aqueous phase can lead to a decrease in conversion. A deficiency of aqueous phase can lead to local temperature spikes which cause decomposition of the cobalt catalyst.

In the prior art, the amount of reaction output withdrawn from the bottom space is determined in accordance with the level of the aqueous bottom phase in the reactor.

EP 1 204 624 B1 discloses a continuous process for hydroformylation of olefins having 6 to 20 carbon atoms wherein a cobalt catalyst-containing aqueous phase is brought into intimate contact with olefins, hydrogen and carbon monoxide in at least one reaction zone (e.g. in a vertical tubular reactor). Reaction output can be withdrawn not only at the top of the reactor but also from the bottom space of the reactor. The withdrawal of reaction output from the bottom space of the reactor is preferably phase regulated.

EP 1 279 658 B1 discloses a process for hydroformylation of olefins having 5 to 24 carbon atoms to produce the corresponding aldehydes and/or alcohols having 6 to 25 carbon atoms in the presence of unmodified cobalt catalysts in a single-step process wherein the aqueous bottom phase is thoroughly mixed in the reactor with the organic phase, the concentration of cobalt compounds in the aqueous bottom phase is in the range from 0.4 to 1.7% by weight and the level of the aqueous bottom phase is kept constant at a steady state.

However, the level of the aqueous bottom phase often cannot be determined accurately under the conditions prevailing in the reactor.

Radiometric measurement of the level of the aqueous bottom phase is imprecise. The γ-radiation is attenuated by passage through the 30 cm-thick steel walls. Additionally, the calibration of the radiometric measurement is difficult since the level of the aqueous bottom phase in the reactor is, as a rule, not known precisely even at calibration.

Further, the maintenance of apparatuses for determining the level of the aqueous bottom phase is very costly and inconvenient when they are disposed inside the reactor and therefore only accessible at great cost and inconvenience by interrupting the process.

The imprecise determination of the level of the aqueous bottom phase leads to an insufficiently precisely controllable withdrawal of aqueous phase from the bottom space and thereby to operational disruptions that ultimately also lower the yield of crude hydroformylation product.

SUMMARY OF THE INVENTION

The object of the present invention is to provide a process for hydroformylation of olefins having 6 to 20 carbon atoms which delivers an increased yield of crude hydroformylation product as a result of stable sustained operation.

The object is achieved by a continuous process for hydroformylation of olefins having 6 to 20 carbon atoms in the presence of a cobalt catalyst in the presence of an aqueous phase with thorough mixing in a reactor wherein a hydroformylation products-containing first stream is withdrawn at the top of the reactor and an aqueous phase-containing second stream is withdrawn from the bottom of the reactor, which process comprises controlling the flow rate of the second stream in accordance with a temperature which is measured at a point in the bottom of the reactor or in a line leading out of the bottom of the reactor.

DETAILED DESCRIPTION OF THE INVENTION

Figure 1:
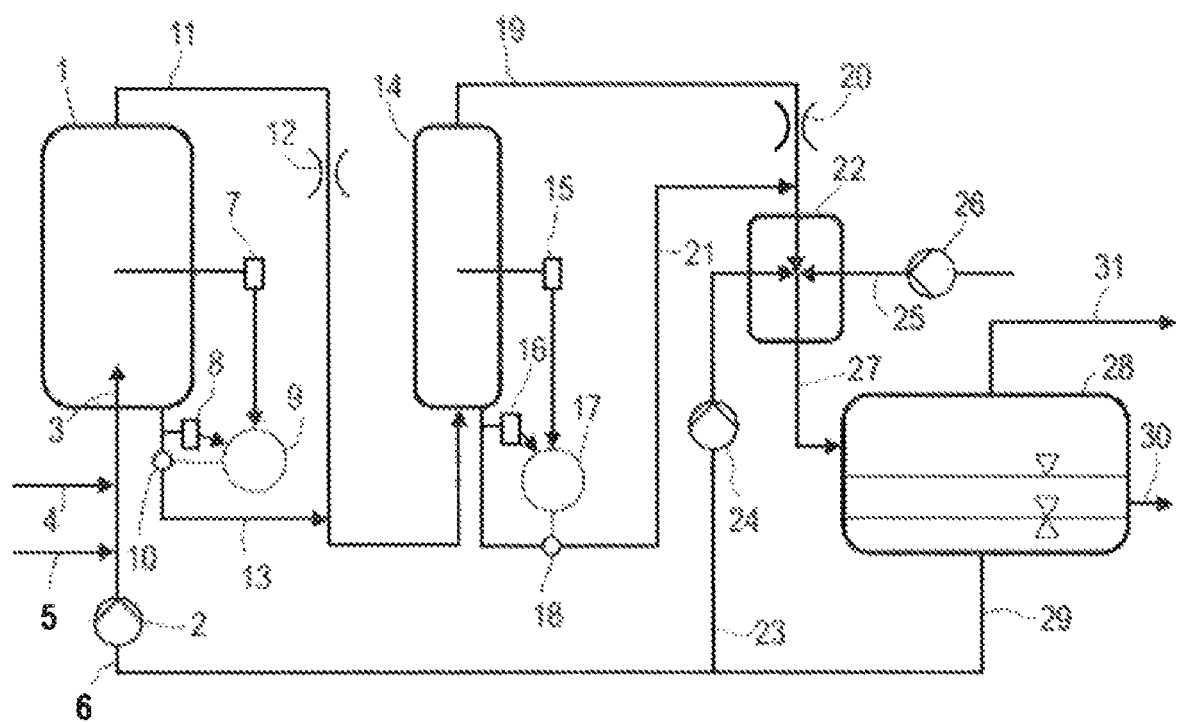
FIG. 1 shows a schematic view of a plant for carrying out the process. The plant comprises a reactor and a post-reactor, in which both the flow rate of the stream withdrawn from bottom of the reactor and the flow rate of the stream withdrawn from the bottom of the post-reactor are controlled in accordance with the invention.

As aqueous phase separates from the organic phase and separates out in the bottom space of the reactor, it no longer undergoes mixing with olefins to be hydroformylated. The reaction rate in the bottom space of the reactor falls and the separated-out aqueous phase slowly cools down. It was found that a stream can be withdrawn from the bottom space of the reactor under temperature control. This prevents the aqueous phase rising to too high a level. The control can also be effected automatically.

The temperature at the point in the bottom of the reactor or in the line leading out of the bottom of the reactor can be accurately determined at minimal cost and inconvenience. Maintenance requirements are also low. Therefore, the number of interruptions of the process due to maintenance of the temperature-measuring apparatus is low, Stable sustained operation is achieved with the process.

As a result of controlling the flow rate of the second stream in accordance with a temperature measured at the point in the bottom of the reactor or in the line leading out of the bottom of the reactor, the temperature measured at the point in the bottom of the reactor or in the line leading out of the bottom of the reactor is available for input, as a control variable, into the control process of the flow rate of the second stream. In addition, other control variables can be captured for input into the control process. Control can be effected by means of computer-based process control. In a control unit, the influence of the change in a correcting variable on one or more control variables can be stored as a mathematical model or algorithm. The measured values of one or more control variables are used to determine correcting interventions for regulating the control variable. Suitable models and programs which can be employed for implementing the present invention will be familiar to a person skilled in the art. In the simplest case, control is carried out manually by the operator adjusting appropriate correcting variables on the basis of a change in the control variable.

When this temperature is measured in the bottom of the reactor, the measurement can be carried out at a point at which the aqueous phase, being the phase of higher specific density, collects. The interior of the reactor is delimited by its floor, lid, and outer wall. The height of the interior extends from the lowest to the highest point of the interior. With regard to the height of the interior, the temperature measurement in the bottom can be carried out for example in the lowermost twentieth, preferably in the lowermost fiftieth of the interior. Preferably, the temperature measurement is carried out at a point below the opening of a supply line through which the olefin and/or other reactants are supplied, e.g. near to the outlet of the aqueous phase-containing second stream.

However, this temperature is preferably measured in a line leading out of the bottom. The line is preferably a line through which the second stream is withdrawn from the bottom of the reactor. In principle, any line that offers a measure of the prevailing temperature in the bottom of the reactor may be used.

In a preferred embodiment, the flow rate of the second stream is controlled in accordance with the difference between the reaction temperature and the temperature measured at the point in the bottom of the reactor or in the line leading out of the bottom of the reactor. Suitably, the reaction temperature is measured at at least one point of vigorous mixing in the reactor. Preferably, the reaction temperature is measured at two or more points of vigorous mixing in the reactor, e.g. at 2, 3, 4, 5 or 6 measuring points, and averaged. Suitable points for measuring the reaction temperature are e.g. the entry points of the olefin or oxogas into the reactor, positions in the immediate vicinity of mixing means in the reactor or near to internals in the reactor for vigorous mixing (e.g. baffles of the reactor contents).

The flow rate of the second stream withdrawn from the bottom of the reactor can be increased when the determinative temperature difference increases. For example, the flow rate of the second stream withdrawn from the bottom of the reactor can be increased when the relevant temperature difference exceeds a first threshold value and decreased when the relevant temperature difference falls below a second threshold value. The second threshold value can be 0 to 5° C. lower than the first threshold value, i.e. both threshold values can be the same. Preferably, both threshold values are selected from a range from 1 to 10° C., preferably 1 to 7° C., particularly preferably 2 to 5° C.

Preferably, the second stream is withdrawn from the bottom of the reactor by passing it out of the bottom of the reactor through a controllable apparatus. The controllable apparatus is preferably a valve. Preferably, the valve is opened as soon as the first threshold value is exceeded, and the valve is closed as soon as the temperature difference falls below the second threshold value. The valve is preferably controlled automatically via a suitable control unit. The control unit calculates the temperature difference and transmits a signal to the valve to open or close dependent on the temperature difference.

Suitable pressure-resistant reactors for carrying out the process according to the invention are known to the person skilled in the art. These include the generally customary reactors for gas-liquid reactions such as e.g. tubular reactors, stirred tanks, gas circulation reactors, bubble columns, loop reactors etc. which, optionally, can be further subdivided by internals, Examples of suitable reactors are a loop reactor, a vertical high-pressure bubble column reactor optionally equipped with coaxial tube-shaped internals, or a vertical tubular reactor. Preferably, the reactor is a vertical bubble column reactor or a vertical tubular reactor.

The temperature in the reactor is generally 100 to 250° C., in particular 145 to 200° C. The prevailing pressure in the reactor is preferably in the region from 100 to 400 bar, particularly 200 to 300 bar.

Part of the reaction mixture contained in the reactor can be discharged in the upper region of the reactor and fed back into the lower region of the reactor in order to vary the thorough mixing. By way of example, the discharged reaction mixture can be passed through a pump and then combined with the starting materials and the starting materials combined with the discharged reaction mixture can be fed into the reactor.

The term "olefins" herein denotes one olefin as well as mixtures of different, e.g. isomeric, olefins. Olefins having 6 to 20 carbon atoms may be hydroformylated by the process according to the invention. The process according to the invention is particularly suitable for the hydroformylation of isomeric olefin mixtures which are prepared by oligomerisation of lower olefins, such as propene and butenes, Typical oligomers useful as olefins for the present process include, inter alia, di-, tri- and tetrapropene, di-, tri- and tetrabutene and co-oligomers of propenes and butenes. The oligomers of butenes are obtainable on a large industrial scale via known oligomerisation processes, e.g. via the Octol process of Hüls and the Dimersol process of IFP. Preference in given to using oligomers based on so-called raffinate 2, a stream containing essentially linear butenes, n- and iso-butane, and not more than 5% by weight of isobutene, preferably not more than 3% by weight of isobutene. Linear long-chain terminal olefins, obtainable e.g. by the SHOP process or Ziegler process, or linear long-chain internal olefins can also be hydroformylated according to the process according to the invention.

The hydroformylation is carried out in the presence of hydrogen and carbon monoxide. The two gases are customarily used in the form of a mixture; so-called synthesis gas. The composition of the synthesis gas used in the process according to the invention can vary between wide limits. The molar ratio of carbon monoxide to hydrogen is, as a rule, about 10:1 to 1:10, in particular 2.5:1 to 1:2.5. A preferable ratio is about 40:60 ($CO:H_2$).

The catalyst extraction and olefin hydroformylation are carried out in one step in the reactor in the process according to the invention. The carbonyl formation can be carried out simultaneously or in an optional upstream catalyst formation step (precarbonylation).

In the optional catalyst formation step (precarbonylation), an aqueous cobalt(II) salt solution is brought into intimate contact with carbon monoxide and hydrogen to form the cobalt catalyst. This is carried out in the presence or absence of the olefins to be hydroformylated, preferably at temperatures of 50 to 200° C., in particular 60 to 140° C. and under pressures of 100 to 400 bar, in particular 200 to 300 bar. The catalyst formation is preferably carried out in apparatus customary for gas-liquid reactions such as stirred tanks equipped with a sparging stirrer, bubble columns or trickle-bed columns. Advantageously, activated charcoal, zeolites or basic ion-exchangers, loaded with cobalt carbonyl, are used in the catalyst formation step as described in DE-OS 21 39 630. The cobalt(II) salts-containing- and cobalt catalyst-containing aqueous solution obtained in the catalyst formation step is then fed into the reactor together with the olefins to be hydroformylated and, optionally, any organic solvents used, as well as hydrogen and carbon monoxide.

The carbonyl formation is particularly advantageously carried out in the upstream catalyst formation step if linear, relatively long-chain terminal olefins are hydroformylated to form predominantly straight-chain aldehydes/alcohols. In order to minimize the formation of undesired branched hydroformylation products, as a rule, lower reaction temperatures are then employed in the reactor. However, under the conditions then employed in the reactor, the active cobalt catalyst is not formed at a sufficient rate.

In many cases, the lower technical requirements make it preferable for the carbonyl formation, catalyst extraction and olefin hydroformylation to be carried out in association with one another in the same reactor. In a preferred embodiment of the process, the formation of the cobalt catalyst, the extraction of the cobalt catalyst into the organic phase and the hydroformylation of the olefins are carried out in association with one another in the same reactor by bringing the aqueous cobalt(II) salt solution, the olefins and, optionally, organic solvents into intimate contact with one another in the reaction zone under hydroformylation conditions.

Irrespective of whether the carbonyl formation is or is not carried out in an upstream catalyst formation step, the starting materials are preferably introduced into the reactor such that good mixing of the phases results and as high as possible an exchange area between the phases is generated. The metering apparatuses known to the person skilled in the art, such as e.g. packed turbulence tubes or mixing nozzles for multiphase systems, can be used for this. The thorough mixing is particularly preferably carried out with a mixing nozzle to maintain a turbulent flow in the reactor. Thorough mixing is carried out in this way in a suitable embodiment by the aqueous cobalt(II) salt solution, olefins, carbon monoxide and hydrogen being simultaneously introduced into the reactor in a circulation system by means of a mixing nozzle as described in DE-AS 12 05 514 and 19 38 102. The optionally used organic solvent is either present in the reactor or is introduced into the reactor simultaneously with the other starting materials, in particular by means of a mixing nozzle.

Optionally usable organic solvents are inert hydrocarbons such as paraffin fractions, aromatic hydrocarbons such as benzene, toluene or xylene, or an aldehyde and/or alcohol; particularly, however, the hydroformylation product of the olefin used. High-boiling by-products of the hydroformylation can further be used as solvent. The use of a solvent can be advantageous in the hydroformylation of long-chain olefins to form long-chain aldehydes, e.g., to lower viscosity.

The first stream, withdrawn at the top of the reactor, in addition to hydroformylation products, comprises unreacted olefins and significant amounts of aqueous phase. The second stream, withdrawn from the bottom of the reactor, can contain, besides aqueous phase, significant amounts of partially reacted organic phase. Preferably, the second stream withdrawn from the bottom of the reactor contains 10 to 80% by volume of aqueous phase.

The described reactor has a so-called stirred tank characteristic; this is a very thoroughly mixed reactor. In such a reactor, only partial conversion is possible with a limited reactor volume. It is therefore preferable, for the purposes of achieving as high a yield as possible of desired product, to continue the hydroformylation and ideally complete the hydroformylation, in a post-reactor. In a preferred embodiment, the first stream and the second stream are fed into a post-reactor.

The temperature in the post-reactor is generally 100 to 250° C., in particular 145 to 200° C. The prevailing pressure in the post-reactor is preferably in the region from 100 to 400 bar, in particular 200 to 300 bar. An even transport of material from the reactor to the post-reactor is preferably effected by the maintenance of a constant differential pressure of a few bar between the reactor and the post-reactor. The differential pressure is preferably 2 to 5 bar. The differential pressure allows convenient control of the discharges from the first reactor. The differential pressure can be maintained by means of an adjustable valve or a diaphragm.

Preferably, at the post-reactor, too, a hydroformylation products-containing first stream is withdrawn at the top and an aqueous phase-containing second stream is withdrawn from the bottom. Preferably, too the second stream withdrawn from the bottom of the post-reactor is withdrawn under temperature control. Thus, in one embodiment, the flow rate of the second stream withdrawn from the post-reactor is controlled in accordance with a temperature measured at a point in the bottom of the post-reactor or in a line leading out of the bottom of the post-reactor. Preferably in accordance with the difference between the reaction temperature in the post-reactor and the temperature at the point in the bottom of the post-reactor or in a line leading out of the bottom of the post-reactor. For the discharging of streams from the post-reactor, the above remarks relating to the first reactor apply correspondingly to the post-reactor. Advantageously, a differential pressure between the post-reactor and the discharge line is set so that the discharges can be well controlled. This can be effected by means of an adjustable valve or a diaphragm. This differential pressure is preferably also from 2 to 5 bar.

In a preferred embodiment, the first and second streams withdrawn from the reactor, or if a post-reactor is used, the first and second streams withdrawn from the post-reactor, are subjected in the presence of aqueous cobalt(II) salt solution to oxygen treatment wherein the cobalt catalyst decomposes to form cobalt(II) salts which are extracted into the aqueous phase and the phases are then separated (decobalting). The streams withdrawn from the reactor and/or post-reactor and optionally combined are appropriately decompressed to intermediate pressure, as a rule 10 to 80 bar, preferably 10 to 50 bar, and then treated with oxygen in the presence of aqueous cobalt(II) salt solution. Preferably, oxygen is provided by supplying air. The treatment is preferably carried out at temperatures of 90 to 130° C. The cobalt(II) salt solution is recycled from the downstream phase separation and is preferably added to the decobalting step with about the same mass flow as the organic output from the (post-)reactor. The cobalt (II) solution is preferably weakly acidic with a pH of 3 to 5, preferably 3.5 to 4.5. The treatment can be carried out in a packed (e.g. with Raschig rings) pressure vessel in which as high as possible an exchange area between the phases is generated, or else by decompression in an empty pressure vessel. The organic product phase is then separated from the aqueous phase, preferably in a downstream phase-separating vessel.

The organic phase remaining after separating off the aqueous phase can then be appropriately worked up, e.g. distilled and/or hydrogenated.

The aqueous phase (cobalt(II) salt solution) is fed into the reactor or into the catalyst formation step or, alternatively, into the decobalting step.

The process according to the invention is illustrated in more detail by the accompanying figures.

FIG. 1 shows a schematic view of a plant for carrying out the process. The plant comprises a reactor and a post-reactor, in which both the flow rate of the stream withdrawn from bottom of the reactor and the flow rate of the stream withdrawn from the bottom of the post-reactor are controlled in accordance with the invention.

As shown in FIG. 1, oxogas 4, olefin 5 and aqueous cobalt (II) salt solution 6 are introduced into a reactor 1 by means of a pump 2 and nozzle 3. The temperature at a point of vigorous mixing in the reactor is measured by means of a thermocouple 7. The temperature in the line leading out of the bottom of the reactor 13 is measured by means of thermocouple 8. The measured temperatures are supplied to the control unit 9. A temperature difference is calculated in control unit 9 by subtracting the temperature measured by means of thermocouple 8 from the temperature measured by means of thermocouple 7. As soon as the temperature difference exceeds a first threshold value, a signal to open the valve 10 emanates from the control unit 9. As soon as the temperature difference falls below a second threshold value, a signal to close the valve 10 emanates from the control unit 9.

A hydroformylation products-containing first stream is withdrawn at the top of the reactor 1 by means of line 11 and passed through diaphragm 12. Provided that valve 10 is open, an aqueous phase-containing second stream is withdrawn from the bottom of the reactor and passed by means of line 13 into line 11.

The combined streams withdrawn at the top and from the bottom of the reactor are introduced into a post-reactor 14 by means of line 11. The temperature at a point of vigorous mixing in the post-reactor is measured by means of thermocouple 15. The temperature in the line 21 leading out of the bottom of the reactor is measured by means of thermocouple 16. The temperatures measured by thermocouples 15 and 16 are supplied to the control unit 17. A temperature difference is calculated in control unit 17 by subtracting the temperature measured by thermocouple 16 from the temperature measured by thermocouple 15. As soon as the temperature difference exceeds a first threshold value, a signal to open valve 18 emanates from the control unit 17. As soon as the temperature difference falls below a second threshold value, a signal to close valve 18 emanates from the control unit 17. A hydroformylation products-containing first stream is withdrawn at the top of post-reactor 14 by means of line 19 and is passed through diaphragm 20. Provided that valve 18 is open, an aqueous phase-containing second stream is withdrawn from the bottom of the post-reactor and passed by means of line 21 into line 19.

The combined streams withdrawn at the top and from the bottom of the post-reactor are introduced by means of line 19 into a hot-decompression vessel 22, which has a lower prevailing pressure than the reactor or the post-reactor and in which they are treated with air supplied by means of line 25 and compressor 26 in the presence of cobalt(II) salt solution which is supplied by means of line 23 and pump 24.

The mixture obtained in the hot-decompression vessel is passed into the phase separator 28 by means of line 27 and an aqueous phase is discharged from the phase separator by means of line 29. The crude hydroformylation product is discharged from the phase separator by means of line 30. Offgas is discharged from the phase separator by means of line 31.

Figure 2:
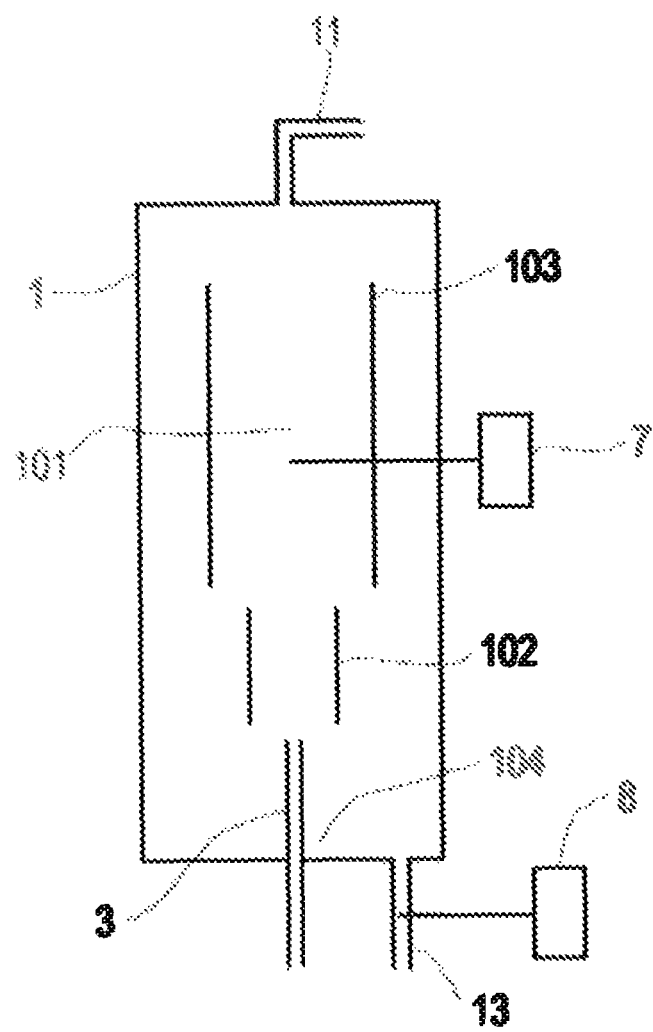
FIG. 2 shows a schematic view of a reactor for carrying out the process according to the invention. The various reference signs have the same meaning as in FIG. 1.

FIG. 2 shows a schematic view of a reactor for carrying out the process according to the invention. The various reference signs have the same meaning as in FIG. 1. The reactor comprises a region of vigorous mixing 101, a mixing zone 102, a post-mixing zone 103, formed by means of cylindrical pipes, and the bottom of the reactor 104. The temperature measured by means of thermocouple 7 is measured at a point in the region of vigorous mixing. The temperature in the line 13 leading out of the bottom of the reactor is measured by means of thermocouple 8.

EXAMPLE

The following parameters were set in a continuous process carried out in a plant according to FIG. 1.

| | |
|---|---|
| oxogas ($CO:H_2$ = 40:60) (4) | 3 300 kg/h |
| isooctene (5) | 10 000 kg/h |
| aqueous cobalt(II) formate solution (6), ca. 1.2% by weight of cobalt | 1 100 kg/h |
| reaction temperature in the reactor (1), measured by thermocouple (7) | 187° C. |
| threshold value for opening and for closing the valve (10) | 2° C. |
| differential pressure between line (11) and line (13) set by means of diaphragm (12) | 4 bar |

-continued

| | |
|---|---|
| reaction temperature in the post-reactor (14), measured by thermocouple (15) | 187° C. |
| threshold value for opening and for closing the valve (18) | 2° C. |
| diameter of the diaphragm (20) in line (19) | 16 mm |
| aqueous cobalt(II) salt solution (23) | 9 000 kg/h |
| air (25) | 50 kg/h |
| offgas (31) | 500 kg/h |

The yield of crude hydroformylation product (30) was 12 400 kg/h.

The invention claimed is:

1. A continuous process for hydroformylation of olefins having 6 to 20 carbon atoms in the presence of a cobalt catalyst in the presence of an aqueous phase with thorough mixing in a reactor wherein a hydroformylation products-containing first stream is withdrawn at the top of the reactor and an aqueous phase-containing second stream is withdrawn from the bottom of the reactor, which process comprises controlling the flow rate of the second stream in accordance with a temperature which is measured at a point in the bottom of the reactor or in a line leading out of the bottom of the reactor.

2. The process according to claim 1, wherein the flow rate of the second stream is controlled in accordance with the difference between a reaction temperature measured at at least one point of vigorous mixing in the reactor and the temperature measured at the point in the bottom of the reactor or in the line leading out of the bottom of the reactor.

3. The process according to claim 1, wherein the flow rate of the second stream is increased when the temperature difference increases.

4. The process according to claim 1, wherein the thorough mixing is carried out by means of a mixing nozzle.

5. The process according to claim 1, wherein the first stream and the second stream are passed into a post-reactor.

6. The process according to claim 5, wherein a hydroformylation products-containing first stream is withdrawn at the top of the post-reactor and an aqueous phase-containing second stream is withdrawn from the bottom of the post-reactor.

7. The process according to claim 6, wherein the flow rate of the second stream withdrawn from the bottom of the post-reactor is controlled in accordance with a temperature measured at a point in the bottom of the post-reactor or in a line leading out of the bottom of the post-reactor.

8. The process according to claim 1 further comprising a catalyst formation step wherein an aqueous cobalt(II) salt solution is brought into intimate contact with carbon monoxide and hydrogen to form the cobalt catalyst.

9. The process according to claim 8, wherein the formation of the cobalt catalyst, the extraction of the cobalt catalyst into the organic phase and the hydroformylation of the olefins are carried out in association with one another in the same reactor by bringing the aqueous cobalt(II) salt solution, carbon monoxide, hydrogen and olefins and, optionally, an organic solvent into intimate contact with one another in the reactor under hydroformylation conditions.

10. The process according to claim 1, wherein the first stream and second stream, withdrawn from the reactor or post-reactor, are subjected in the presence of aqueous cobalt (II) salt solution to oxygen treatment wherein the cobalt catalyst decomposes to form cobalt(II) salts which are extracted into the aqueous phase and the phases are then separated.

11. The process according to claim 10, wherein part of the aqueous phase is recycled into the reactor or is brought into intimate contact with carbon monoxide and hydrogen to form the cobalt catalyst.

12. The process according to claim 1, wherein the reactor is a vertical tubular reactor.

13. The process according to claim 1, wherein the second stream withdrawn from the reactor or post-reactor comprises 10 to 80% by volume of aqueous phase.

* * * * *